United States Patent [19]

Schwabe

[11] Patent Number: 5,322,688

[45] Date of Patent: Jun. 21, 1994

[54] METHOD OF PREPARATION OF AN EXTRACT FROM GINKGO BILOBA LEAVES AND PHARMACEUTICALS CONTAINING THE EXTRACT

[75] Inventor: Klaus-Peter Schwabe, Karlsruhe, Fed. Rep. of Germany

[73] Assignee: Dr. Willmar Schwabe GmbH & Co., Karlsruhe, Fed. Rep. of Germany

[21] Appl. No.: 899,016

[22] Filed: Jun. 15, 1992

Related U.S. Application Data

[63] Continuation of Ser. No. 624,177, Dec. 4, 1990, abandoned.

[30] Foreign Application Priority Data

Dec. 4, 1989 [DE] Fed. Rep. of Germany ....... 3940092

[51] Int. Cl.$^5$ .................... A61K 35/78; A61K 31/70
[52] U.S. Cl. ..................... 424/195.1; 514/27
[58] Field of Search .......... 424/195.1; 514/27

[56] References Cited

U.S. PATENT DOCUMENTS

| | | | |
|---|---|---|---|
| 4,708,949 | 11/1987 | Liu | 514/27 |
| 4,753,929 | 6/1988 | Matsumoto | 514/27 |
| 4,886,904 | 12/1989 | Tanaka | 560/249 |
| 4,892,883 | 1/1990 | Chatterjee | 514/464 |
| 4,981,688 | 1/1991 | Ayroles | 424/195.1 |

FOREIGN PATENT DOCUMENTS 0324197  7/1989  European Pat. Off. ......... 424/195.1

OTHER PUBLICATIONS

Naranishi, Roji The Ginkgolides Butterworth & Co. England, 1967 pp. 89-110.
Gellerman J. L. Analytical Chemistry vol. 40 No. 4 Apr. 1968, pp. 739-743.
The Merck Index 11th Ed. Merck & Co. Rahway N.J. #4320.
Maruyama, M., et al. "The Ginkgolides I. Isolation and Characterization of the Various Groups" Tetra. Lett. No. 4, pp. 299-302 (1967).
Okabe, K., et al. "Gingkolides" J. Chem. Soc. pp. 2201-2206 (1967).
Nakanishi, K., et al. J. Am. Chem. Soc. 93: 3544-3547 (1971).
Gellerman, J. L. Phytochem. 15: 1959-1961 (1976).
Hill, G. A. et al., J. Am. Chem. Soc. 56: 2736-2738 (1934).
Sowers, W. F. et al., Arch. Derm. 91: 452-456 (1965).
Nakamura, T. Contact Derm. 12: 281-282 (No. 5, 1985).
Becker, L. E. et al. J. Am. Med. Assoc. 231: 1162-1163 (No. 11, 1975).

Primary Examiner—Michael G. Wityshyn
Assistant Examiner—Ralph G. Gitomer
Attorney, Agent, or Firm—Kenyon and Kenyon

[57] ABSTRACT

The invention relates to a method of preparation of an improved extract from Ginkgo biloba leaves and to pharmaceuticals containing the extract.

12 Claims, No Drawings

METHOD OF PREPARATION OF AN EXTRACT FROM GINKGO BILOBA LEAVES AND PHARMACEUTICALS CONTAINING THE EXTRACT

This application is a continuation of application Ser. No. 07/624,177, filed on Dec. 4, 1990, now abandoned.

The invention relates to a method of preparation of an improved extract from *Ginkgo biloba* leaves and to pharmaceuticals containing the extract.

Extracts from the leaves of *Ginkgo biloba* have been used for a long time for the therapy of peripheral and cerebral arterial circulatory disturbances. Methods of preparation of *Ginkgo biloba* extracts with a greatly enriched content of flavone glycosides as the active components are known; see DE-B 17 67 098 and DE-B 21 17 429. These extracts are also referred to as *Ginkgo biloba* monoextracts.

EP-A 0 324 197 describes a method of preparation of an extract from *Ginkgo biloba* leaves in which an aqueous solution of a lower alcohol or ketone, obtained after extraction of the leaves, is concentrated in the presence of kieselguhr. The resultant aqueous suspension is filtered through kieselguhr, the fitrate is extracted with butanone and the extract is freed from the solvent.

EP-A 330 567 relates to a method of preparation of an extract from *Ginkgo biloba* leaves in which the crushed leaves extracted with an aqueous ketone compound. This extract is concentrated until biflavones and hydrophobic compounds precipitate. After filtration the aqueous concentrate is rendered alkaline, whereby the proanthocyanidins precipitate. After separation of the precipitate and acidification of the filtrate, a liquid-liquid-extraction is carried out with a $C_{4-6}$-ketone compound in the presence of ammonium sulfate. The extract is obtained after stripping of the ketone compound.

DE-A 35 14 054 has disclosed that the ginkgolides, known components of the *Ginkgo biloba* leaves which are terpenoid substances with lactone structure (see K. Nakanishi, Pure and Applied Chemistry, Vol. 14 (1967), 89–113, and M. Maruyama et al., Tetrahedron Letters (1967), 299–302 and 303–319, and K. Okabe et al., J. Chem. Soc. (1967), 2201–2206), can be used to treat illnesses and similar conditions caused by PAF ("Platelet Activating Factor").

The use of bilobalide, a further substance contained in the *Ginkgo biloba* leaves, is known from DE-A 33 38 995 and the corresponding U.S. Pat. No. 4 571 407 for the treatment of demyelinating neuropathies, encephalopathies and cerebral edemas. Bilobalide is a sesquiterpene lactone structurally related to ginkgolides (see K. Nakanishi et al., R. T. Major et al., and K. Weinges et al., J. Am. Chem. Soc., Vol. 93 (1971), 3544–3546).

Besides the compounds mentioned above, *Ginkgo biloba* leaves also contain so-called ginkgolic acids (anacardic acids). These compounds are 6-alkylsalicylic acids with n-$C_{13}$- to n-$C_{19}$-alkyl groups with 0 to 3 double bonds; see J. L. Gellermann et al., Phytochemistry, Vol. 15 (1976), 1959–1961 and Analytic. Chem., Vol. 40 (1968), 739–743.

"Ginkgol", a phenol substituted with the corresponding alkyl group, can be obtained either biogenetically by decarboxylation of the ginkgolic acids or during the technical processing of the *Ginkgo biloba* leaves; see Kawamura, Japan, J. Chem., Vol. 3 (1928), 91–93.

The ginkgolic acids and ginkgols in *Ginkgo biloba* are accompanied by corresponding derivatives with a further phenolic hydroxyl group in 4-position, the 6-alkylresorcylic acids or 5-alkylresorcins; see J. Gellermann et al., Phytochemistry, Vol. 15 (1976), 1959–1961. These resorcin derivatives are responsible for the toxic effects and especially for the strong allergies and contact dermatitis caused by toxicodendron plants; see G. A. Hill et al., J. Am. Chem. Soc., Vol. 56 (1934), 2736–2738.

Cases of strong allergic reactions after contact with Ginkgo fruits are known; see W. F. Sowers et al., Arch. Dermatol., Vol. 91 (1965), 452–456, and T. Nakamura, Contact Dermatitis, Vol. 12 (1985), 281–282. Serious mucosal disturbances after eating Ginkgo fruits have been described; see L. E. Becker and G. B. Skipworth, J. Am. Med. Assoc., Vol. 231 (1975), 1162–1163. Allergic skin reactions also occur occasionally on collecting or handling Ginkgo leaves.

The significance of allergies caused by alkylphenol compounds from anacardiaceae and ginkgoaceae is evident from the development of substances and methods of desensitisation described in patent literature (see U.S. Pat. No. 4 428 965) against the allergies caused by alkylphenol compounds.

Commercial extracts from *Ginkgo biloba* leaves contain between 50 and 10,000 ppm ginkgolic acids.

The extracts from *Ginkgo biloba* leaves prepared by the known methods in DE-B 17 67 098 and DE-B 21 17 429 are substantially free of alkylphenol compounds because the lipophilic components of the extract are removed by a liquid-liquid-extraction of the aqueous acetone extract with a substantially water-immiscible lipophilic solvent, e.g. with a chlorinated aliphatic lower hydrocarbon such as carbon tetrachloride. However, in this step, the therapeutically valuable ginkgolides and the bilobalide are also considerably reduced so that their content in the final product in Example 1 of DE-B 21 17 429 is a maximum of 0.5% in the case of ginkgolides A, B, C and J in total and approximately 0.3% in the case of bilobalide. The quantity of flavone glycosides, however, is greatly increased during this step, namely from 3 to 4% in the crude extract to approximately 24% in the final product.

The object of the present invention is to provide a method of preparation of the extract from *Ginkgo biloba* leaves which is substantially free of alkylphenol compounds and which has a high content of flavone glycosides, ginkgolides and bilobalide. The method of the present invention should, in contrast to the known methods in DE-B 17 67 098 and DE-B 21 17 429, succeed in removing the alkylphenol compounds without the use of chlorinated aliphatic hydrocarbons. The use of chlorinated hydrocarbons in technical processes is very problematic because of the occupational medical risks, the potential danger of these compounds to the environment and the possibility of undesirable residues in pharmaceuticals.

A further advantage of the method of the present invention compared to the method in DE-B 21 17 429 is that no lead compounds are used in the removal of the undesirable polyphenol compounds with tanning properties (proanthocyanidins). Compounds of lead are most undesirable because of the health risks for the people involved, and over and above that, the costs involved for their proper disposal are considerable.

It is a further object of the invention to provide pharmaceuticals which contain this *Ginkgo biloba* extract with a high content of flavone glycosides, ginkgolides and bilobalide and where there is substantially no danger of allergic reactions, precisely because of the removal of the alkylphenol compounds.

The invention therefore relates to a method of preparation of this *Ginkgo biloba* extract from *Ginkgo biloba* leaves which comprises the steps described in claims 1-4. In contrast to the method of separating the lipophilic components described in DE-B 17 67 098, the aqueous alcohol or aqueous acetone crude extract is not directly subjected to liquid-liquid-extraction with a chlorinated aliphatic hydrocarbon, but rather most of the lipophilic components, which precipitate on distillation of the organic solvent components and dilution with water to a maximum content of 10 weight percent, preferably 5 weight percent, are separated by filtration. The alkylphenol compounds, the chlorophyll, the fatty acid derivatives and the biflavones precipitate due to their low solubility in water and can be separated by filtration. Under these conditions, the desired components of the *Ginkgo biloba* extract remain dissolved.

Subsequently, the methylethylketone or methylethylketone/acetone-extracts are prepared according to DE-B 17 67 098 and DE-B 21 17 429. In contrast to the method in DE-B 21 17 429, however, a lead compound or a polyamide is not used to reduce the content of proanthocyanidins to less than 10%, but rather a distribution of the butanone extract is carried out between water and a water-immiscible $C_{4-5}$-alkanol, whereby the proanthocyanidins remain in the water phase.

In a preferred embodiment the extraction with methylethylketone or methylethylketone/acetone is directly replaced by extracting the aqueous extract solution freed from the lipophilic components with a water-immiscible alkanol of 4 or 5 C-atoms. For economic reasons *n*-butanol is preferred. 10 to 30 weight percent of sodium chloride or ammonium sulfate can be added to the aqueous extract solution. The alkylphenol compounds are reduced further to a content of less than 10 ppm in a subsequent decreasing step by removing the solvent from the butanol or pentanol extract by distillation, preparing a solution with 5 to 20 weight percent solids content in 20 to 60 weight percent of aqueous ethanol and subjecting this solution to a multistep liquid-liquid-extraction with an aliphatic hydrocarbon with a boiling point of 60° to 100° C.

In addition, the invention relates to pharmaceuticals which according to claim 5 are characterized by a content of *Ginkgo biloba* extract.

In pharmacological experimental models, the extract prepared according to the present invention has radical scavenging properties and properties which stimulate the circulation of blood, prevent ischemic disorders and inhibit platelet aggregations.

The *Ginkgo biloba* extract of the invention can be processed in the usual way for the preparation of pharmaceuticals e.g. to solutions, coated tablets, tablets or injection preparations. The pharmaceuticals in the invention are used for the treatment of peripheral and cerebral arterial circulatory disturbances.

The examples illustrate the invention. Parts and percentage data refer to weight unless otherwise stated.

EXAMPLE 1

100 kg of dry *Ginkgo biloba* leaves are crushed in a mill to a particle size of less than 4 mm. After adding 750 kg of 60 weight percent aqueous acetone the mixture is stirred intensively for 30 minutes at a temperature of 57° to 59° C. The solid residue is separated by filtration or centrifugation and subjected to a second extraction under the same conditions. The extracts from the first and second extraction steps are combined. The ginkgolic acid content (based on the dry extract) equals approximately 13,000 ppm. The resultant extract is concentrated under reduced pressure to a solids content of 30 to 40% and a maximum of approximately 5 weight percent acetone. By adding water, the concentrate is diluted to double volume and, while being stirred, left to cool to approximately 12° C. A precipitate forms which contains most of the ginkgolic acids, that is, the alkylphenol compounds, present in the leaves. After one hour at this temperature, the resultant precipitate is separated by centrifugation and discarded.

The ginkgolic acid content in the resultant aqueous supernatant (based on the dry extract) equals approximately 320 ppm.

30 parts of ammonium sulfate are added to 100 parts of the aqueous solution. The mixture is stirred. After the ammonium sulfate has dissolved, a liquid-liquid-extraction is carried out twice with a mixture of methylethylketone and acetone in a ratio of 6:4 to 1:1, whereby the organic solvent added is equivalent to half the volume of the aqueous solution and, after intensive stirring and pumping, the organic upper phase formed on completion of the mixing process is removed.

The methylethylketone acetone solution is then concentrated under reduced pressure to a solids content of 50 to 70%. This concentrate is diluted with water to a solids content of 10%. This substantially aqueous extract solution is stirred three times, each time with half of its volume of water-saturated *n*-butanol. The combined butanol phases are concentrated under reduced pressure to a solids content of at least 50%. To remove the *n*-butanol from the highly concentrated extract by azeotropic distillation, water, preferably, is added. The resultant aqueous concentrate is diluted with water and ethanol so that a solution with 10 weight percent dry extract in 30 weight percent aqueous ethanol is obtained.

To reduce the alkylphenol compounds to a residual content of less than 10 ppm, this solution is stirred at least three times at room temperature, each time with ⅓ of its volume of *n*-heptane.

The water phase is concentrated under reduced pressure to a solids content of at least 50% and dried at a maximum product temperature of approximately 60° to 80° C. to a dry extract with a water content of less than 5%.

From 100 kg of Ginkgo leaves, 2.7 kg of *Ginkgo biloba* extract with a content of 24.8 weight percent flavone glycosides, 3.2% ginkgolides, 2.9% bilobalide, approximately 5% proanthocyanidins and less than 1 ppm alkylphenol compounds are obtained.

EXAMPLE 2

The aqueous extract solution obtained in Example 1, following separation by centrifugation of the precipitate consisting predominantly of lipophilic components, is stirred three times, each time with half of its volume of butan-2-ol (sec. butylalcohol).

The resultant butan-2-ol solution is evaporated under reduced pressure until a concentrate with at least 50% solids content is obtained. Preferably water is added to remove the butanol from the highly concentrated extract by azeotropic distillation. Following dilution with water and ethanol to a solids content of approx. 10% and approx. 30 percent by weight ethanol in the solution, the solution is stirred three times, each time with ⅓ of its volume of cyclohexane.

The water phase is concentrated under reduced pressure to a solids content of at least 50% and dried at a maximum temperature of 60° to 80° C. to a dry extract with a water content of less than 5%.

From 100 kg of Ginkgo leaves, 2.9 kg of *Ginkgo biloba* extract with a content of 25.3% flavone glycosides, 3.4% ginkgolides, 3.1% bilobalide, approximately 4.2% proanthocyanidins and less than 1 ppm alkylphenol compounds are obtained.

EXAMPLE 3

Solution for oral administration:

| 100 ml solution contains: | |
|---|---|
| Ginkgo biloba extract | 4.0 g |
| ethanol | 50.0 g |
| demineralised water to | 100.0 ml |

EXAMPLE 4

Coated tablets:

| tablet contains: | | |
|---|---|---|
| Ginkgo biloba extract | | 40.00 mg |
| microcrystalline cellulose | | 100.00 mg |
| lactose | | 80.00 mg |
| colloidal silicic acid | | 25.00 mg |
| talcum (in core) | | 4.50 mg |
| magnesium stearate | | 0.50 mg |
| hydroxypropyl methylcellulose | | 12.00 mg |
| ferric oxide pigment | | 0.10 mg |
| talcum (in coat) | | 0.50 mg |
| weight of a coated tablet | approx. | 262.60 mg |

I claim:

1. A method of preparing an extract from the leaves of *Ginkgo biloba* which is substantially free of alkylphenol compounds and having a high content of flavone glycosides and comprising substantially all of the ginkgolides and bilobalide originally present in the leaves, the method comprising the steps of
   a) extracting the leaves with an organic solvent selected from the group consisting of aqueous acetone, an aqueous alkanol having one to three carbon atoms and anhydrous methanol;
   b) separating most of the organic solvent from the extract of step (a) by evaporation or distillation, optionally at reduced pressure, to form an aqueous solution;
   c) diluting the aqueous solution with water to a solids content of 5 to 25 weight percent;
   d) cooling the diluted aqueous solution to precipitate and remove the water-insoluble lipophilic components from the diluted aqueous solution;
   e) treating the aqueous solution from step (d) with 10-30% ammonium sulfate then extracting the aqueous solution with a solvent selected from the group consisting of methylethylketone and a mixture of methylethylketone and acetone;
   f) extracting the extract from step (e) with butanol or pentanol;
   g) diluting the butanol or pentanol extract from step (f) with water and alcohol to form an aqueous alcohol solution;
   h) extracting the aqueous alcohol solution with an aliphatic or cycloaliphatic solvent having a boiling point of about 60°–100° C. to further remove the alkylphenol compounds; and
   i) concentrating the aqueous extract solution resultant from step (h) under reduced pressure and drying the resultant concentrate at a maximum temperature of 60° to 80° C. to form a dry extract with a water content of less than 5 weight percent.

2. A method of preparing an extract from *Ginkgo biloba* leaves, containing 20 to 30 weight percent flavone glycosides, 2.5 to 4.5 weight percent of ginkgolides A, B, C and J, 2.0 to 4.0 weight percent bilobalide, less than 10 ppm alkylphenol compounds and less than 10 weight percent proanthocyanidins comprising the steps of:
   (a) extracting fresh or dried green leaves of *Ginkgo biloba* at a temperature of approximately 40° to 100° C. with an organic solvent selected from the group consisting of aqueous acetone, an aqueous alkanol of 1 to 3 C-atoms and anhydrous methanol;
   (b) vacuum distilling the extract from step (a) to remove the organic solvent to a maximum content of 10 weight percent to form a concentrated aqueous solution;
   (c) diluting the concentrated aqueous solution with water to a solids content of 5 to 25 weight percent then cooling the diluted aqueous solution to a temperature below 25° C. to precipitate and remove the water-insoluble lipophilic components from the diluted aqueous solution;
   (d) adding ammonium sulfate to the aqueous solution from step (c) to a concentration of 30 weight percent and extracting said solution with a solvent selected from the group consisting of methylethylketone and a mixture of methylethylketone and acetone in a ratio from about 9:1 to 4:6;
   (e) concentrating the extract from step (d) to a solids content of 50 to 70% then diluting with water to a solids content of about 10 weight percent;
   (f) extracting the aqueous concentrate from step (e) with water-immiscible $C_4$ or $C_5$ alkanol to form alkanol layers;
   (g) concentrating the alkanol layers to a solids content of 50 to 70 weight percent;
   (h) diluting the concentrate of step (g) with water and ethanol to form a solution having 5 to 20 weight percent dry extract in 20 to 60 weight percent aqueous ethanol;
   (i) extracting the aqueous alcohol solution from step (h) with an aliphatic or cycloaliphatic solvent having a boiling point of about 60° to 100° C. to further remove alkylphenol compounds;
   (j) concentrating the aqueous extract solution resultant from step (i) under reduced pressure and drying the resultant concentrate at a maximum temperature of 60° to 80° C. to form a dry extract with a water content of less than 5 weight percent.

3. The method of claim 2 wherein the dry extract contains about 22 to 26% by weight flavone glycosides.

4. The method of claim 2 wherein the dry extract contains less than 1 ppm alkylphenol compounds.

5. The method of claim 2 wherein the concentrated aqueous solution of step (b) contains a maximum of 5 weight percent organic solvent.

6. The method of claim 2 wherein the solids content of step (c) is about 15 to 20% by weight.

7. The method of claim 2 wherein the diluted aqueous solution of step (c) is cooled to about 10° to 12° C.

8. The method of claim 2 wherein the methylethylketone and acetone mixture of step (d) is in a ratio of 6 to 4.

9. The method of claim 2 wherein the alkanol of step (f) is *n*-butanol or pentanol.

10. A method of preparing an extract from *Ginkgo biloba* leaves, containing 20 to 30 weight percent flavone glycosides, 2.5 to 4.5 weight percent of ginkogolides A, B, C and J, 2.0 to 4.0 weight percent bilobalide, less than 10 ppm alkylphenol compounds and less than 10 weight percent proanthocyanidins comprising the steps of:

(a) extracting fresh or dried green leaves of *Ginkgo biloba* at a temperature of approximately 40° to 100° C. with an organic solvent selected from the group consisting of aqueous acetone, an aqueous alkanol of 1 to 3C-atoms and anhydrous methanol;

(b) vacuum distilling the extract from step (a) to remove the organic solvent to a maximum content of 10 weight percent to form a concentrated aqueous solution;

(c) diluting the concentrated aqueous solution with water to a solids content of 5 to 25 weight percent, and then cooling the diluted aqueous solution to a temperature below 25° C. to precipitate and remove the water-insoluble lipophilic components from the diluted aqueous solution;

(d) extracting the aqueous extract solution from step (c) with a water-immiscible $C_4$ to $C_5$ alkanol layer said aqueous solution optionally containing 10 to 30 weight percent of sodium chloride or ammonium sulfate;

(e) concentrating the alkanol layer to a solids content of 50 to 70 weight percent;

(f) diluting the concentrate of step (e) with water and ethanol to form a solution having 5 to 20 weight percent dry extract in 20 to 60 weight percent aqueous ethanol;

(g) extracting the aqueous ethanol solution from step (f) with an aliphatic or cycloaliphatic solvent having a boiling point of about 60° C. to 100° C. to further remove alkylphenol compounds;

(h) concentrating the aqueous extract solution from step (g) under reduced pressure;

(i) drying the resultant concentrate from step (h) at a maximum temperature of 60° C. to 80° C. to form a dry extract with a water content of less than 5 weight percent.

11. The method of claim 10 wherein the alkanol of step (d) is *n*-butanol or pentanol.

12. A pharmaceutical composition comprising a *Ginkgo biloba* extract prepared according to the process of any one of claims 1, 2 and 10 in a pharmaceutical carrier.

* * * * *

UNITED STATES PATENT AND TRADEMARK OFFICE
CERTIFICATE OF CORRECTION

PATENT NO. : 5,322,688
DATED : June 21, 1994
INVENTOR(S) : Klaus-Peter SCHWABE

It is certified that error appears in the above-indentified patent and that said Letters Patent is hereby corrected as shown below:

| Column | Line | |
|--------|------|---|
| 1 | 29 | After "leaves" insert --are--. |
| 5 | 26 | Before "tablet" insert --1--. |
| 6 | 19 | Change "3C-atoms" to --3 C-atoms--. |
| 7 | 17 | Change "3C-atoms" to --3 C-atoms--. |
| 8 | 2 | Change "to" to --or--; after "layer" insert --,--. |

Signed and Sealed this

Fifteenth Day of November, 1994

Attest:

BRUCE LEHMAN

Attesting Officer    Commissioner of Patents and Trademarks